United States Patent [19]

Sampson

[11] 4,190,048
[45] Feb. 26, 1980

[54] INFUSATE INJECTION APPARATUS

[75] Inventor: Edward J. Sampson, Concord, Mass.

[73] Assignee: Metal Bellows Corporation, Sharon, Mass.

[21] Appl. No.: 924,623

[22] Filed: Jul. 14, 1978

[51] Int. Cl.² ............................................ A61M 5/00
[52] U.S. Cl. ............................ 128/215; 128/218 NV
[58] Field of Search ....... 128/218 NV, 218 N, 218 D, 128/218 DA, 218 F, 218 R, 215, 216, 221, 272.3, 274

[56] References Cited

U.S. PATENT DOCUMENTS

| | | | |
|---|---|---|---|
| 2,709,433 | 5/1955 | Sorenson | 128/218 NV |
| 2,816,550 | 12/1957 | Hudson | 128/215 X |

Primary Examiner—John D. Yasko
Attorney, Agent, or Firm—Cesari and McKenna

[57] ABSTRACT

Apparatus for injecting infusate into a reservoir implanted in the human body comprises a housing from which projects a hollow needle. The needle is slidably mounted in the housing and spring biased to its extended position in which the inner end of the needle is closed by a valve. The needle is extended and locked during injection through the skin and septum of an implanted reservoir, after which the needle lock is released to permit automatic function of the apparatus when the needle hits a stop behind the septum. The resultant needle setback opens the valve permitting fluid to flow through the needle into the reservoir.

3 Claims, 2 Drawing Figures

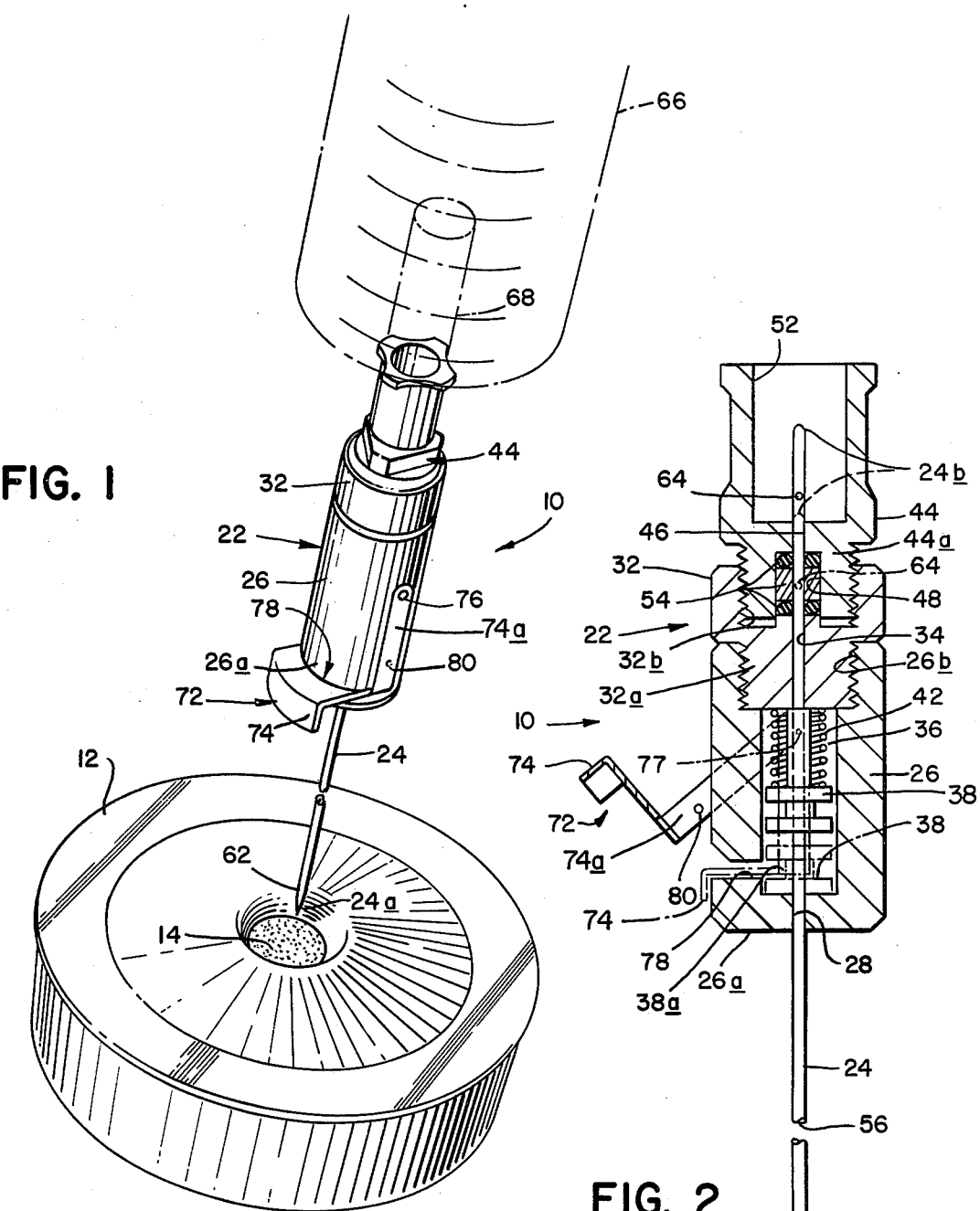
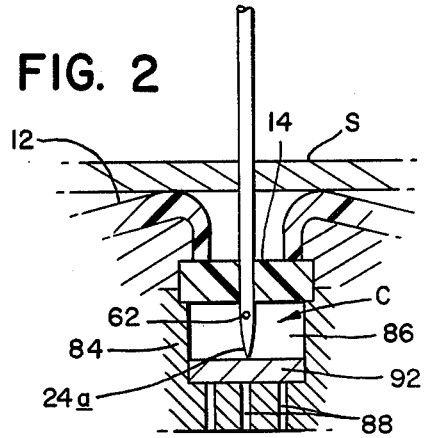

INFUSATE INJECTION APPARATUS

This invention relates to fluid injection apparatus. It relates more particularly to apparatus for injecting infusate subcutaneously through a septum into a reservoir implanted in the human body.

BACKGROUND OF THE INVENTION

Recently there has been perfected an implantable prosthetic device in the nature of an infusate pump or so-called artificial gland for dispensing infusates such as durgs and hormones at a very low flow rate to a selected site in the human body over the long term. Eventually the fluid reservoir in such a pump empties so that, if the pump is to continue performing its function, its reservoir must be refilled with a fresh supply of infusate. To avoid having to operate on a patient to remove the pump in order to refill it periodically, the pump is designed with a penetrable self-sealing septum in a wall of the pump which normally seals a passage leading to the pump reservoir.

With the pump implanted in the patient's body so that the septum underlies the skin, the pump can be refilled, as needed, simply by injecting a fresh supply of infusate by means of a hypodermic needle through the patient's skin, through the pump septum and into the infusate chamber inside the device. In some cases, the act of refilling the pump also recharges its power supply so that the pump can operate uninterruptedly for a prolonged period. Implantable pumps such as this are disclosed, for example, in U.S. Pat. Nos. 3,731,681 and 3,851,147.

It is apparent from the foregoing that if the pump is to have a long service life after it is implanted in the body, the penetrable septum must be capable of retaining its sealing properties even after a large number of injections. In other words, the hypodermic needle used to inject the infusate into the pump must not "core" the septum so as to create possible avenues of leakage therethrough.

Also, it is essential that the needle end of the infusate injection apparatus be seated at the proper charging location in the pump before infusate flow is commenced. By the same token, the flowing needle must not be pulled out of the septum as the refilling operation proceeds. Otherwise, the infusate being injected may not flow into the pump reservoir as it is supposed to. Rather, it may be deposited locally in the patient's body. Accordingly, unbeknownst to the patient and the physician, the pump may not be refilled completely and may therefore run out of infusate prematurely with possible adverse consequence to the patient. Additionally, the deposition of a relatively large quantity of infusate locally into the patient might also prove detrimental to the patient.

Bearing in mind that such implantable devices actually move to some extent in the patient's body and that the pump may be situated at different depths below the skin depending upon the weight of the patient, properly seating and maintaining the needle end of the injection apparatus in the pump's recharging station is not a simple matter using a standard hypodermic syringe.

SUMMARY OF THE INVENTION

Accordingly it is an object of the present invention to provide a septum-penetrating infusion apparatus designed specifically to refill infusate reservoirs implanted in the body.

Another object of the invention is to provide such infusate injection apparatus which can penetrate the septum in the implanted device many times without adversely affecting the sealing properties of the septum.

Still another object of the invention is to provide infusate injection apparatus of this type which does not permit infusate flow unless the apparatus is seated properly at the charging station of the implanted device.

Still another object of the invention is to provide infusate injection apparatus of this general type which is relatively simple to make and easy to maintain.

Other objects will in part be obvious and will in part appear hereinafter.

The invention accordingly comprises the features of construction, combination of elements and arrangement of parts which will be exemplified in the following detailed description, and the scope of the invention will be indicated in the claims.

Briefly, the infusate injection apparatus comprises a pencil-like housing from which projects a long hollow needle. The needle is slidably mounted in the housing and biased toward an extended position at which it projects substantially beyond the end of the housing. The needle has the usual small longitudinal passage characteristic of hypodermic needles. However, that passage is closed at both ends of the needle and transverse passages are formed through the needle at locations spaced from the opposite ends of the needle which passages intercept the main longitudinal passage. When the needle is in its extended position, the transverse passage openings at the inner end of the needle are blocked by a seal mounted in the housing so that there is no fluid flow from points upstream of the seal into the needle.

However, when the needle is retracted in opposition to the spring bias, the passage openings at the inner end of the needle are uncovered from the seal so that fluid is free to flow into and through the needle. A lock is also provided on the housing for preventing needle setback so that the needle remains in its extended position until the lock is released.

In use, the needle of the infusion apparatus is injected through the patient's skin at the site of the septum in the implanted device while the needle is locked in its extended position so that the needle cannot retract as it penetrates the patient's skin and the septum. When the pointed end of the needle is properly located inward of the septum at the charging station of the implanted device, it bottoms against a needle stop at the station. At this point, the needle lock is released so that further movement of the housing toward the patient causes the needle to move toward its retracted position thereby unsealing the inner end of the needle so that infusate under pressure is free to flow through the needle into the device's charging station.

If the pointed end of the needle moves away from the needle stop to any significant degree as, for example, when the patient or the physician moves, the needle will immediately be urged by its spring to its extended position thereby sealing the inner end of the needle and interrupting the flow of infusate. Accordingly, there is little likelihood of infusate being discharged inadvertently directly into the patient because the needle is not seated properly in the implanted device.

Since the openings near the pointed end of the needle are on the side of the needle rather than at the end thereof, they present no sharp edges that might tend to core the septum. Consequently,, such apparatus can be used to refill an implantable device of this type many times, over a prolonged period, without degrading its septum to such an extent that the device has to be removed and repaired.

The present apparatus is also relatively simple to make and easy to assemble and use. Therefore, it should find wide application whenever implanted fluid reservoirs have to be refilled and/or recharged.

BRIEF DESCRIPTION OF THE DRAWING

For a fuller understanding of the nature and objects of the invention, reference should be had to the following detailed description taken in connection with the accompanying drawing in which:

FIG. 1 is a fragmentary perspective view of the infusate injection apparatus shown in conjunction with an implantable pump; and FIG. 2 is a sectional view with parts in elevation showing the FIG. 1 apparatus injecting infusate subcutaneously into an implanted pump.

DESCRIPTION OF THE PREFERRED EMBODIMENT

Referring now to FIG. 1 of the drawings, the infusate injection apparatus of this invention is indicated generally at 10. It is arranged to inject infusate into an implanted prosthetic device such as pump 12 by way of the pump's penetrable septum 14. Pump 12 is completely described in the aforesaid patents and will not be detailed here. Of course, the apparatus 10 could also be used to inject infusate into any other kind of fluid reservoir that may be implanted in the human body.

Turning now to FIGS. 1 and 2, the injection apparatus 10 comprises a cylindrical housing shown generally at 22 from one end of which projects a long, thin, hollow needle 24. Housing 22 is actually composed of three sections. More particularly, it has an end or bottom section 26, one end 26a of which is closed except for a tiny opening 28 for slidably receiving needle 24. The upper end 26b of that section is internally threaded to receive the threaded end 32a of a bushing 32 comprising the second section of housing 22. Bushing 32 also has an axial passage 34 for slidably receiving needle 24.

Housing section 26 and bushing 32 define a cavity 36 inside the housing through which needle 24 passes. A collar 38 is secured to needle 24 inside cavity 36 and a coil spring 42 is compressed between that collar and the bushing end 32a so as to bias the needle 24 to an extended position wherein the collar 38 engages against the housing section end 26a as shown in dotted lines in FIG. 2.

With the needle in its extended position, the needle end 24b extends from the bushing passage 34 and projects slightly beyond the end of the bushing. A threaded bore 32b is formed in bushing 32 for receiving the threaded end 44a of a Lure-lock type fitting 44 comprising the third section of housing 22. Fitting 44 has an axial passage or bore 46 for slidably receiving needle 24. Also the fitting has a relatively small diameter counterbore 48 extending inward from its end adjacent bushing 32. A second counterbore 52 extends in from the opposite end of the same fitting. Seated in counterbore 48 are annular seals 54 made of silicone rubber or other sturdy resilient material.

Needle 24 has the usual longitudinal passage 56. However, that passage does not extend at the opposite ends of the needle. Rather, the opposite ends 24a and 24b of the needle are closed, the former making a sharp point, and a pair of transverse passages 62 and 64 respectively are drilled through the needle at locations spaced from the ends thereof so that the passages intercept the longitudinal passage 56. The openings into passage 62 are located on the side walls of the needle so that there are no sharp edges presented to septum 14 when the needle is injected through the septum. On the other hand, the openings into passage 64 near the inner end of the needle are situated inside counterbore 48 when the needle is in its extended position shown in dotted lines in FIG. 2 so that the passage 64 openings are completely blocked by the seals 54. Consequently, fluid cannot flow from counterbore 52 into the needle.

However, when the needle 24 is moved to its retracted position, shown in solid lines in FIG. 2, in opposition to the bias afforded by spring 42, the inner end of the needle and passage 64 are moved out of counterbore 48 and bore 46 into counterbore 52 away from the seals 54 so that fluid is now free to flow from counterbore 52, into passage 64, through the needle and be discharged from the passage 62 adjacent the pointed end of the needle.

The Lure-lock female fitting 44 is coupled to a standard Lure-lock male fitting connected to the end of a suitable infusate-containing syringe 66 or conduit 68 as shown in FIG. 1.

Preferably also, a lock indicated generally at 72 is provided to lock the needle 24 in its extended position in which the needle passage 64 is closed off by seals 54. The illustrated embodiment, lock 72 comprises a clip 74 adjacent the closed end of housing section 26. The clip has a pair of long spaced-apart arms 74a extending along the outside of housing section 26. A pair of short, inwardly projecting pins 76 are attached to the ends of arms 74a (one is shown in FIG. 1), which pins project into appropriate small openings 77 (FIG. 2) in the sides of housing section 26 so that the clip 74 can pivot relative to the housing. Actually the clip can be swung between a locked position shown in FIG. 1 wherein it engages collar 38 in the end of housing section 26 through slot 78 and an unlocked (flowing) position shown in solid lines in FIG. 2 wherein the clip is retracted out of collar 38 and the slot 78. The clip is retained in the locked position by dimples 80 on arms 74a engaging in mating dimples in housing section 26. When the clip 74 is in its locked position, it fits in a necked down portion 38a of collar 38 secured to needle 24 so that the needle cannot be moved to its retracted position. On the other hand, when the clip is swung to its released position away from collar 38, the needle 24 is free to retract into housing 22 to unseal the needle passage 64.

In order to refill pump 12, the needle 24 is injected through septum 14 into the pump's charging station C. In FIG. 2, the station is illustrated as a small cylindrical cup 84 defining an antechamber 86 lying just below septum 14. Small passages 88 are provided in the bottom wall of cup 84 so that fluid injected into antechamber 86 pass through those openings into the pump 12 reservoir (not shown). A discoid needle stop 92 made of polytetrafluoroethylene or other strong yet soft material is positioned against the bottom wall of antechamber 86.

When the pump 12 is implanted in a human, it is situated so that its septum 14 is disposed underneath the skin layers S. In order to refill the pump when it is nearly empty of infusate, the injection apparatus 10 is connected to a source of infusate such as the hose 68 or hypodermic syringe 66. Then with the clip 74 in its locked position illustrated in FIG. 1, the needle 24 is injected through the patient's skin S and through septum 14. When the pointed end of the needle 24a bottoms against the needle stop 92, the resistance of the apparatus to further injection is sensed by the physician.

Thereupon, the physician moves clip 74 to its released position shown in FIG. 2 and pushes the housing 22 further toward the patient. This further movement of the housing results in needle 24 setback so that the needle retracts into the housing in opposition to the bias of spring 42 until the passage 64 at the inner end of the needle clears passage 46 as shown in solid lines in FIG. 2. At this point, infusate present in the housing counterbore 52 is free to flow into passage 64, through the needle and discharge through the passage 62 openings into antechamber 86.

If the patient moves or the physician moves, the needle 24 will not retract through the septum without first shutting off the flow of infusate through the needle. This is because as soon as the needle pulls away from needle stop 92, it moves toward its extended position. If that movement continues to any appreciable extent, the needle extends until its inner passage 64 is closed by seals 54 as shown in dotted lines in FIG. 2 stopping further flow before the needle can be inadvertently withdrawn from the septum. Consequently, the physician knows that whenever fluid is flowing through the apparatus, it is being discharged into the antechamber 86 of pump 12 as it should be, and not being discharged locally into the patient in the vicinity of the pump. Thus if a measured amount of infusate corresponding to the capacity of the pump reservoir is injected through apparatus 10, it is assured that the pump reservoir is completely refilled so that the pump's supply of infusate is not exhausted prematurely. It is further assured that a large quantity of infusate is not inadvertently injected locally into the patient's body.

The fact that the passage 62 openings adjacent the pointed end of the needle are located well away from the needle point protects the septum 14 from being cored by sharp edges as the needle penetrates the septum. Consequently, repeated injections by the apparatus 10 should not adversely affect the septum. Resultantly, the pump 12 can remain implanted in the patient's body for a prolonged period, being refilled and recharged periodically during its lifetime in the body.

As best seen from FIG. 2, the apparatus 10 is easily assembled simply by screwing together the various housing sections 26, 32 and 44 after inserting the needle 24 through the passage 28 in housing section 26. Likewise, the seals 54 can be replaced easily whenever that is necessary simply by unscrewing the housing section 44 from the bushing 32.

It will thus be seen that the objects set forth above among those made apparent from the preceding description are efficiently attained, and since certain changes may be made in the above construction without departing from the scope of the invention, it is intended that all matter contained in the above description or shown in the accompanying drawing shall be interpretted as illustrative and not in a limiting sense.

It should also be understood that the following claims are intended to cover all of the generic and specific features of the invention herein described.

I claim:

1. Apparatus for injecting infusate percutaneously through a septum into an infusate chamber implanted in a body comprising:
   A. a housing,
   B. a needle projecting from the housing, said needle having a longitudinal passage,
   C. means for slidably mounting the needle in the housing so that it is movable between an extended positon and a retracted position,
   D. means for biasing the needle toward its extended position,
   E. means for conducting fluid into the housing, and
   F. valve means in the housing for controlling the flow of fluid from the housing into the needle, said valve means being closed when the needle is in its extended position and said valve means being open when the needle is in its retracted position whereby fluid infusate cannot flow through the needle unless the exposed end of the needle bottoms against a stop in the chamber thereby facilitating moving the needle to its retracted position, said valve means comprising:
      1. a transverse passage through the needle near its inner end, said transverse passage intercepting the longitudinal passage through the needle, and
      2. a resilient seal mounted in the housing so as to cover the ends of said transverse passage when the needle is in its extended position, the ends of said transverse passage being free of said seal when the needle is in its retracted position.

2. Apparatus for injecting infusate percutaneously through the septum of a fluid reservoir of a device implanted in a body comprising:
   A. means in the implanted device inward of the septum defining a chamber,
   B. a needle stop positioned at the inner end of the chamber,
   C. a housing,
   D. a hollow needle projecting from the housing, said needle having a longitudinal passage closed at both ends,
   E. means for slidably mounting the needle in the housing so that the needle is movable between an extended position and a retracted position,
   F. means for biasing the needle towards its extended position, and
   G. transverse passages extending through the needle near its ends, said passage intercepting said longitudinal passage, and
   H. annular sealing means mounted in the housing so as to engage around the inner end of the needle and cover the transverse passage when the needle is in its extended position, said transverse passage being retracted from and free of the sealing means when the needle is moved toward its retracted position whereby when the needle is injected through the septum and engages the needle stop inside the implanted device, the needle is set back to its retracted position thereby exposing the transverse passage so that fluid introduced into the housing can enter the needle and be discharged from its outer end into the chamber and when the apparatus is retracted away from the needle stop, the needle is moved toward its extended position so that the transverse passage is closed by said sealing means whereby that fluid cannot be discharged inadvertently inside the body exteriorly of the implanted device.

3. Apparatus for injecting infusate percutaneously through a septum into an infusate chamber of a device implanted in a body comprising:
   A. a housing,
   B. a needle projecting from the housing, said needle having a longitudinal passage,
   C. means for slidably mounting the needle in the housing so that it is movable between an extended position and a retracted position,
   D. means for biasing the needle toward its extended position,
   E. means for conducting fluid into the housing,
   F. means in the implanted device inward of the septum defining a chamber,
   G. a needle stop positioned at the inner end of the chamber, and
   H. valve means in the housing for controlling the flow of fluid from the housing into the needle, said valve means being closed when the needle is in its extended position and said valve means being open when the needle is in its retracted position whereby when the needle is injected through the septum and engages the needle stop inside the implanted device, the needle is set back to its retracted position thereby opening the valve means so that fluid introduced into the housing can enter the needle and be discharged from its outer end into the chamber and when the apparatus is retracted away from the needle stop, the needle is moved towards its extended position so that the valve is closed whereby fluid cannot be discharged inadvertently inside the body exteriorly of the implanted device.

* * * * *